United States Patent [19]

Baetz

[11] 4,172,118

[45] Oct. 23, 1979

[54] DIPHENYLAMINE CONTAINING THERAPEUTIC COMPOSITION AND ITS APPLICATIONS, PARTICULARLY IN VETERINARY MEDICINE

[75] Inventor: Jacques L. E. Baetz, La Garenne Colombes, France

[73] Assignee: METABIO, Meudon la Foret, France

[21] Appl. No.: 818,836

[22] Filed: Jul. 25, 1977

[30] Foreign Application Priority Data

Aug. 4, 1976 [GB] United Kingdom ............... 32542/76

[51] Int. Cl.$^2$ ............................................. A61K 31/135
[52] U.S. Cl. ....................................... 424/10; 424/330
[58] Field of Search .......................................... 424/10

[56] References Cited

PUBLICATIONS

H. Gordon et al., Chemical Abstracts, 34:8049$^3$, 1940.
Merck Veterinary Manual, Fourth Edition, (1973), pp. 702–704.
A. Mackie, et al., Chemical Abstracts, 49:11181a, (1955).
S. Zarinskaya, et al., Chemical Abstracts, 85:41000y, (1976).
A. Banting, et al., Chemical Abstracts, 83:157857w, (1975).
W. Spector (ed.), Handbook of Biological Data, 1956, pp. 506–508.
A. Banchetti, Chemical Abstracts, 50:15949d, 1956, Research on Anthelmintic Drugs.
J. Guthrie, Chemical Abstracts, 35:197$^9$, 1941, Preliminary Observations on the Efficacy of Diphenylamine for the Removal of Intestinal Nematodes from Dogs.

Primary Examiner—Donald G. Daus
Assistant Examiner—M. C. Eakin
Attorney, Agent, or Firm—Young & Thompson

[57] ABSTRACT

The invention concerns the use of diphenylamine as a detoxicant for halogen-containing drugs administered to animals, such as carbon tetrachloride, hexachlorophene, bithionol sulfoxide, etc. The diphenylamine may be administered separately to the animal or simultaneously with the halogen-containing drug in the form of a therapeutic composition.

6 Claims, No Drawings

DIPHENYLAMINE CONTAINING THERAPEUTIC COMPOSITION AND ITS APPLICATIONS, PARTICULARLY IN VETERINARY MEDICINE

Diphenylamine is already used in synthetic chemistry as an intermediate for the synthesis of numerous molecules such as the phenothiazines, in particular.

Various pharmacological properties of this compound are disclosed in the literature, such as the anticonvulsant activity (C.A., Vol. 54 17708g) and the antiparasitic activity (C.A., Vol. 50-15949d).

Its action against certain myases (Merck Index, 8th Ed., p. 387) in animals and against certain Nematodes in dogs (C.A., Vol. 35, 197, 9) is also disclosed.

The experiments conducted by Applicant, a detailed description of which is given hereinafter together with the results obtained, demonstrate a further pharmacological property of this compound, viz., a detoxicant property in animals with respect to some halogen-containing agents, particularly chlorine-containing agents, used in veterinary medicine, typically as antiparasitic drugs.

Thus, this invention relates to a novel application of diphenylamine as a detoxicant with respect to halogen-containing drugs, such as are typically used in veterinary medicine.

This provides a new application of diphenylamine in combination with drugs such as $CCl_4$, hexachlorophene, bithionol sulfoxide, and the like.

The invention includes also within its scope a new therapeutic composition comprising diphenylamine in combination with one or more halogen-containing drugs, such as mentioned above, the therapeutic activity of which was known, but the toxicity of which limited their use.

By means of the new composition of this invention, a more complete therapeutic activity may be obtained in the treatment of diseases for which such various drugs are applicable, particularly in the treatment of parasitic diseases, due to an improved tolerance in animals and to the use of higher dosages of active ingredients.

According to an embodiment of this invention, the halogen-containing drugs and diphenylamine are administered separately, diphenylamine being preferably administered prior to the halogen-containing drug, typically by the oral route.

According to another embodiment, the halogen-containing drug and the diphenylamine are administered simultaneously as a therapeutic composition containing both said components, optionally together with a therapeutically administrable carrier.

In either case, diphenylamine is used in an amount of 0.1–10 wt% with respect to the halogen-containing drug, said amounts varying within said range depending on the nature of the halogen-containing drug used.

Thus, for example, said amount will advantageously be 0.5–5% in the case of hexachlorophene, 2–10% in the case of bithionol sulfoxide, 1–5% in the case of carbon tetrachloride, etc.

The therapeutic composition of this invention may be administered by the oral, sub-cutaneous, intramuscular or percutaneous routes and will optionally include suitable carriers and excipients for such routes of administration.

For oral administration, the composition may be formulated as capsules (with or without carrier), pastes, or as aqueous or oily solutions or suspensions. For parenteral or sub-cutaneous administration, solutions in preferably non-aqueous solvents (such as dimethylformamide, olive oil, paraffin oil, and the like) are used.

Illustrative formulations of the therapeutic composition of this invention are given below.

| A - Hexachlorophene/Diphenylamine containing compositions | |
|---|---|
| 1. Capsules | |
| for 1 capsule: | |
| hexachlaorophene | 500 mg |
| diphenylamine | 7.5 mg |
| (administrable at a rate of 1 capsule per 25 kg body weight at an immaturicidal dosage of 20 mg/kg) | |
| 2. Tablets | |
| for 1 scored tablet: | |
| hexachlorophrene | 500 mg |
| diphenylamine | 7.5 mg |
| magnesium stearate | 18 mg |
| talc | 186 mg |
| glycerol tripalmito-stearate | 72 mg |
| dicalcium phosphate | 336.5 mg |
| crystalline cellulose (Avicel Ph 102) | 880 mg |
| | 2000 mg |
| 3. Paste | |
| hexachlorophene | 20 g |
| diphenylamine | 0.3 g |
| sodium saccharinate | 0.32 g |
| Carbopol 941 | 1.60 g |
| 1N sodium hydroxide, sufficient to pH 5 | |
| distilled water, sufficient to make (i.e. 76 ml) | 100 ml |
| 4. Suspension | |
| hexachlorophene | 40 g |
| diphenylamine | 0.6 g |
| Carbopol 941 | 1.50 g |
| sodium saccharinate | 0.64 g |
| 1N sodium hydroxicde, sufficient amount to pH 5 | |
| distilled water, sufficient amount to make | 1000 ml |

| B - Bithionol sulfoxide (BTS)/Diphenylamine containing compositions | |
|---|---|
| 1. Capsules | |
| bithionol sulfoxide | 1500 mg |
| diphenylamine | 75 mg |
| (administrable at a rate of 1 capsule per 25 kg body weight at an immaturicidal dosage of 60 mg/kg BTS, or per 37.5 kg body weight at a conventional dosage of 40 mg/kg). | |
| 2. Tablets | |
| bithionol sulfoxide | 2 g |
| diphenylamine | 0.1 g |
| wheat starch | 0.235 g |
| glycerol tripalmito stearate | 0.065 g |
| magnesium stearate | 0.035 g |
| polyvinyl pyrrolidone | 0.065 g |
| | 2.5 g |
| 3. Paste | |
| bithionol sulfoxide | 40.00 g |
| diphenylamine | 2.00 g |
| sodium Nipagine | 0.10 g |
| sodium saccharinate | 0.32 g |
| Carbopol 941 | 1.60 g |
| propylene glycol, sufficient amount to make | 100 ml |
| 4. Suspension | |
| bithionol sulfoxide | 80 g |
| diphenylamine | 4 g |
| Carbopol 941 | 1.5 g |
| Rhodorsil 426 R | 0.180 g |
| Tartrazine dye | 0.025 g |
| sodium methyl paraben | 0.80 g |

-continued

| B - Bithionol sulfoxide (BTS)/Diphenylamine containing compositions | |
|---|---|
| sodium propyl paraben | 0.20 g |
| Polysorbate 80 | 0.50 g |
| Caustic soda | 0.25 g |
| 95% ethyl alcohol | 0.25 g |
| distilled water, sufficient amount to make | 1000 ml |

A summary of the experiments conducted in animals is given below for illustrative purposes. The efficiency of diphenylamine as detoxicant for the chlorine-containing drugs administered will be apparent therefrom.

1. Hexachlorophene is an antiparasitic agent which has been widely used in verterinary medicine, but which has been abandoned in many countries, in spite of its high therapeutic effectiveness, in view of its low chemotherapeutic coefficient.

Acute toxicity tests were conducted in mice. The death rate noted in mice administered hexachlorophene alone was compared with that noted in mice which were administered the same dosages of hexachlorophene, but which had previously been protected by administration of diphenylamine.

Ten groups of 10 male mice each were used in such experiments. Five reference groups were given hexachlorophene alone, at increasing dosages. The five other groups were administered diphenylamine at a dosage of 1.5 mg/kg one-half hour prior to administration of the same hexachlorophene dosages as the reference animals. Both compounds were administered orally, using peanut oil as the excipient.

The data relating to the death rate variations in both groups, with respect to the dosages of compound used, are set forth in the following Table.

| | Death Rate (%, 7 days after administration of the test materials) | |
|---|---|---|
| Dosages of hexachlorophene used (mg/kg) | Group administered hexachlorophene alone | Group Administered hexachlorophene + diphenylamine at a dosage of 1.5 mg/kg |
| 109.6 | 10% | 0% |
| 128.2 | 20% | 0% |
| 150 | 20% | 10% |
| 175.5 | 40% | 20% |
| 205.3 | 60% | 20% |

As is apparent from this Table, the addition of diphenyl amine reduces the hexachlorophene-induced acute toxicity in mice.

2. Bithionol sulfoxide is one of the more widely used antiparasitic agents in veterinary medicine.

The acute toxicity of bithionol sulfoxide was compared with that of a combination of 20 parts bithionol sulfoxide per part diphenylamine.

Ten groups of 10 male mice each were used for this test. Five reference groups were administered increasing dosages of bithionol sulfoxide alone. The five other groups were administered the bithionol sulfoxide + diphenylamine combination. The test materials were administered orally.

The data relating to the death rate variations in both groups, with respect to the dosages of product used, are set forth in the following Table.

As is apparent from this Table, the addition of diphenylamine reduces the bithionol sulfoxide-induced acute toxicity in mice.

| Death rate (%) noted 7 days after administration of the test materials | | | |
|---|---|---|---|
| Bithionol sulfoxide dosage (mg/kg) | Diphenylamine dosage (mg/kg) | Group I without diphenylamine | Group II with diphenylamine |
| 450 | 22.5 | 0% | 0% |
| 600 | 30 | 10% | 0% |
| 800 | 40 | 20% | 0% |
| 1066 | 53 | 40% | 10% |
| 1420 | 71 | 30% | 10% |

3. To demonstrate the protective effect of diphenylamine with respect to the hepato-toxicity of carbon tetrachloride, a conventional test procedure is used; the pentobarbital-induced sleeping test in mice. This test provides a measure of the capability of the liver to metabolize some toxic materials. The principle is as follows: in normal mice, a certain sleeping time is induced by a certain dosage of pentobarbital; in mice which have been administered 48 hours previously a hepato-toxic material, the same pentobarbital dosage induces a longer sleeping time, because the injured liver has greater difficulty in metabolizing pentobarbital; on administration of a supposedly detoxicant material 24 hours after the toxic material, one may examine whether sleeping time is reduced or not and, thus, may quantify the resulting protection.

This test is effected using carbon tetrachloride as toxicant at a dosage of 0.075 ml/kg, and diphenylamine as protective material at a dosage of 4 mg/kg. The following results are obtained:

| | Reference group | Unprotected group $CCl_4$ | Protected group $CCl_4$ + diphenylamine |
|---|---|---|---|
| Sleeping time | 20 mn | 109 mn | 74 mn |

It is apparent from the above results that sleeping-time is indeed reduced by the administration of diphenylamine.

4. Two groups of non-pregnant Ile-de-France ewes, weighing from 46 to 68 kg, were intoxicated with carbon tetrachloride administered sub-cutaneously at a dosage of 3600 mg/kg, as a suspension in vaseline oil.

The second group alone was simultaneously administered diphenylamine at a dosage of 100 mg/kg.

The criterion used to evaluate the magnitude of the intoxication was the variation of the serum glutamic oxalacetic transaminase (S.G.O.T.) level.

In the following Table, the percent increase of said serum levels is given with respect to the level determined prior to the intoxication.

| | Group I Unprotected group $CCl_4$ | Group II Protected group $CCl_4$ + diphenylamine |
|---|---|---|
| Percent S.G.O.T. increase | 91% | 35% |

It is apparent from the above Table that the S.G.O.T. level increases in a significantly reduced manner in the group protected with diphenylamine.

5. Two groups of non-pregnant Limousin ewes, weighing from 45 to 52 kg, were intoxicated with hexachlorophene at a dosage of 90 mg/kg, administered orally; whereas the generally used therapeutic dosage is 10 mg/kg.

The clinical signs, and particularly the variation of the weight curve, were noted over a 5 day period of time.

One of the groups was simultaneously administered 2 mg/kg diphenylamine, by the same route of administration.

In the unprotected group, a sustained state of exhaustion was noted in the animals throughout the observation period and, in one animal of the group, convulsions were observed. General loss of weight was noted. Indeed, while the average weight was 48.6 kg prior to the administration, it was 41.66 kg after five days, i.e., a decrease of 14.38% of the weight within five days.

In the protected group, no clinical sign was noted, except for a rapid exhaustion of only 24 hours duration. No loss of weight was noted: the average weight remained stable at 47.5 kg.

It is apparent from the above data that weight stabilization and the most substantial reduction of the clinical signs are due to the administration of diphenylamine.

6. Two groups of five healthy sheep were artificially infested with a substantial amount of liver flukes (*Fasciola hepatica*).

Twenty-eight days after the infestation, one of said groups was treated with hexachlorophene and diphenylamine at the respective dosages of 20 mg/kg hexachlorophene and 0.23 mg/kg diphenylamine, by the oral route.

All the animals were sacrificed 3 months after infestation.

The adult flukes found at the level of the liver of each animal were counted.

|  | Number of flukes remaining after 3 months (average number per animal) |
|---|---|
| Reference group | 30 |
| Treated group | 13 |

The fasciolicidal activity of hexachlorophene is maintained when the compound is combined with diphenylamine.

7. Six groups of 5 sheep each were orally intoxicated with increasing dosages of hexachlorophene (135–142.5–150 mg/kg) with or without diphenylamine.

As will be apparent from the following Table, the addition of diphenylamine induces a significant decrease of the death rate, and this at dosages which attain a very high level.

| Number of sheep | Diphenylamine (mg/kg) | Hexachlorophene (mg/kg) | Number of sheep killed |
|---|---|---|---|
| 5 | 0 | 135 | 1 |
| 5 | 0 | 142.5 | 4 |
| 5 | 0 | 150 | 5 |
| 5 | 1.58 | 135 | 0 |
| 5 | 1.67 | 142.5 | 2 |
| 5 | 1.76 | 150 | 3 |

Having now described my invention what I claim as new and desire to secure by Letters Patent is:

1. Process for the detoxification of a drug selected from the group consisting of carbon tetrachloride, hexachlorophene and bithionol sulfoxide in animals, comprising administering diphenylamine to an animal given said drug by the oral, subcutaneous, intramuscular or percutaneous route in an amount of 0.1–10 weight percent with respect to the weight of said drug.

2. Process as claimed in claim 1, wherein the diphenylamine is administered simultaneously with said drug.

3. Process as claimed in claim 1, wherein the diphenylamine and said drug are administered separately.

4. Therapeutic composition useful in veterinary medicine for the treatment of liver flukes, comprising a drug selected from the group consisting of carbon tetrachloride, hexachlorophene and bithionol sulfoxide and diphenylamine as a detoxicant in an amount of 0.1–10 weight percent with respect to the weight of said drug.

5. Composition as claimed in claim 6, in unit dosage form.

6. Process as claimed in claim 3, in which the diphenylamine is administered prior to said drug.

* * * * *